United States Patent
Hofmann et al.

(10) Patent No.: US 11,340,364 B2
(45) Date of Patent: May 24, 2022

(54) PROVIDING AN ITEM OF CONVERSION INFORMATION RELATING TO AN IMAGE DATASET

(71) Applicant: Siemens Healthcare GmbH, Erlangen (DE)

(72) Inventors: Christian Hofmann, Erlangen (DE); André Ritter, Neunkirchen am Brand (DE)

(73) Assignee: Siemens Healthcare GmbH, Erlangen (DE)

( * ) Notice: Subject to any disclaimer, the term of this patent is extended or adjusted under 35 U.S.C. 154(b) by 270 days.

(21) Appl. No.: 16/383,557

(22) Filed: Apr. 12, 2019

(65) Prior Publication Data
US 2019/0317231 A1    Oct. 17, 2019

(30) Foreign Application Priority Data
Apr. 13, 2018   (EP) ..................... 18167300

(51) Int. Cl.
*G01T 7/00*         (2006.01)
*A61B 6/00*         (2006.01)

(52) U.S. Cl.
CPC .............. *G01T 7/005* (2013.01); *A61B 6/583* (2013.01)

(58) Field of Classification Search
CPC ......... A61B 6/032; A61B 6/583; A61B 6/482; A61B 6/542; A61B 6/584; A61B 6/025; A61B 6/5205; A61B 6/4241; A61B 6/502; A61B 6/405; A61B 6/4441; A61B 8/4494; A61B 5/055; A61B 6/582; A61B 8/5207;
(Continued)

(56) References Cited

U.S. PATENT DOCUMENTS

2004/0077088 A1   4/2004  Charles, Jr.
2014/0072108 A1*  3/2014  Rohler ............... A61B 6/488
                                                378/207
(Continued)

FOREIGN PATENT DOCUMENTS

WO   WO20020238045 A2   5/2002
WO   WO2008046498 A1   4/2008

OTHER PUBLICATIONS

European Search Report for European Patent Application No. 18167300.5-1124 dated Oct. 15, 2018.
(Continued)

*Primary Examiner* — Ajibola A Akinyemi
(74) *Attorney, Agent, or Firm* — Lempia Summerfield Katz LLC

(57) ABSTRACT

A method for providing an item of conversion information describing an allocation rule of at least one physical property value of a material in a voxel relating to an image value of the voxel in a three-dimensional image dataset recorded with an X-ray apparatus is provided. By scanning a phantom including at least one calibration material in the X-ray apparatus, a calibration database that is used for determining the allocation rule is determined. The image dataset is recorded with a receiving spectrum geared to an X-ray detector of the X-ray apparatus. The receiving spectrum is described by at least one spectral parameter. For determining the allocation rule dependent upon the spectral parameter, calibration data derived from the measured calibration dataset describing different receiving spectra is used.

19 Claims, 3 Drawing Sheets

(58) Field of Classification Search
CPC ..... A61B 6/0407; A61B 6/4085; A61B 6/488; A61B 8/085; A61B 8/5223
USPC ........................................................ 382/128
See application file for complete search history.

(56) References Cited

U.S. PATENT DOCUMENTS

2014/0236488 A1    8/2014  Brown
2018/0113227 A1*   4/2018  Lin ......................... G01T 7/005

OTHER PUBLICATIONS

Schneider, Uwe, Eros Pedroni, and Antony Lomax. "The calibration of CT Hounsfield units for radiotherapy treatment planning." Physics in Medicine & Biology 41.1 (1996): 111-124.
Witt, Matthias, et al. "Optimization of the stopping-power-ratio to Hounsfield-value calibration curve in proton and heavy ion therapy." Zeitschrift für Medizinische Physik 25.3 (2015): 251-263.

* cited by examiner

PROVIDING AN ITEM OF CONVERSION INFORMATION RELATING TO AN IMAGE DATASET

This application claims the benefit of EP 18167300.5, filed on Apr. 13, 2018, which is hereby incorporated by reference in its entirety.

BACKGROUND

The present embodiments relate to providing an item of conversion information describing an allocation rule of at least one physical property value of a material in a voxel relating to an image value of the voxel in a three-dimensional image dataset.

In different contexts, it has been proposed to derive physical property values of materials (e.g., in the field of medical technology of a patient) from three-dimensional image datasets of an X-ray apparatus (e.g., a computed tomography apparatus), since the attenuation coefficients contained as image information in the three-dimensional image datasets (e.g., Hounsfield Unit (HU) values) relate to such physical property values (e.g., values that bear directly upon the attenuation properties of the material). For example, if background information regarding the materials in the scanning region is already available, different physical property values may thus be concluded. Different X-ray apparatuses have different recording properties. The actually obtained attenuation coefficients in an image dataset may additionally be dependent on recording parameters for recording the image dataset and on properties of the recorded object (e.g., a patient). Known methods for determining an allocation rule for obtaining, from attenuation values for a voxel, the physical property value of the material contained therein have already been proposed (e.g., to record a calibration dataset on a phantom that contains defined materials, for which information regarding the imaging of the attenuation properties is obtained). Since physical information is also present for these materials, allocation rules on physical property values may be derived as conversion information.

Whereas such conversion information may be used in many application fields (e.g., with regard to a calcium scoring and/or in hybrid modalities), radiation therapy or, specifically, planning of the radiation therapy may be cited as a significant application field of such allocation rules. Particularly with regard to the use of particulate radiation (e.g., proton irradiation), physical property values that may be derived from X-ray recordings (e.g., computed tomography recordings) are to be taken into account for treatment at the correct location. An exemplary comparison of different conversion approaches regarding particle therapy is found in an article by M. Witt et al., "Optimization of the stopping-power-ratio to Hounsfield-value calibration curve in proton and heavy ion therapy," Z. Med. Phys. 25(3), pages 251 to 263, 2015, which specifically deals with the determination of the stopping power as a physical property value from HU values. The stoichiometric calibration also discussed therein is fundamentally described in an article by U. Schneider et al., "The calibration of CT Hounsfield units for radiotherapy treatment planning," Phys. Med. Biol. 41 (1996), pages 111 to 124.

In an application of the physical property values in the irradiation planning, typically a dose distribution that is to be expected is determined based upon the irradiation. The distribution of the physical property value in the patient ascertainable based on the conversion information, where the physical property value may represent, for example, the electron density, the mass density, and/or the stopping power, is used to describe the energy deposition by the radiation in the patient and accordingly to optimize the energy deposition with regard to the therapy goal. Typically, computed tomography recordings of the patient in the position that may also be used for irradiation are used as image datasets.

It is known in the prior art to carry out the conversion of the image values, specifically HU values, in the image datasets into the physical property values using a conversion table as the conversion information. This conversion table is generated by a computed tomography scan on a phantom, as described in the introduction. A suitable phantom may contain a plurality of calibration materials that simulate the bandwidth of the body tissue in relation to the physical property value and the image value. The allocation resulting from the calibration scan between physical size and image value may be adopted directly as an allocation rule.

The aforementioned stoichiometric calibration enables greater accuracies to be achieved, whereby the values of the phantom scan are not adopted directly. Rather, an analytical model of the resultant image values dependent upon the density and stoichiometric composition of a material is used. The model contains free parameters that are stipulated dependent upon the calibration scan on the phantom. The calibration materials used in the phantom are not subject to the restriction of being as similar as possible to tissue, but rather, calibration materials where, although the calibration materials have a certain similarity to materials occurring in the body with regard to stoichiometric composition, the composition of the calibration materials is, however, exactly known and may be reproduced well with the mathematical model, may be utilized. If the free model parameters of the model are known, then based on the known stoichiometric composition of real human tissue, a conversion table or another allocation rule may again be created and stored (e.g., in a planning device for the planning of the radiation therapy).

In the prior art, the allocation rules, and therefore the conversion information, are typically stored directly in the planning device (e.g., a planning system with which the irradiation planning is to be carried out). Herein, the problem exists that the HU values are not universal for all X-ray apparatuses and all the usable X-ray spectra. Storage of a large number of conversion information items for different devices, spectra, and the like in the planning device, however, would be associated with too great an effort. There also exists the problem that the patient himself has a "filtering" effect to a certain extent, which may affect the spectrum received by the X-ray detector of the X-ray apparatus and thus the HU values. Properties of the X-ray apparatuses may also change with age. Particularly in particle irradiation, for example, the use of protons or other ions where a hard cut-off edge in the energy deposition exists, an extremely precise pre-calculation of the dose distribution is essential in order, for example, to be able to treat a tumor as exactly as possible, so that such relatively small differences may also be crucial.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the simple provision of highly accurate conversion information adjusted to the patient and/or the X-ray apparatus used is provided.

The image dataset is recorded with a receiving spectrum geared to an X-ray detector of the X-ray apparatus. The receiving spectrum is described by at least one spectral parameter, whereby for determining the allocation rule dependent upon the spectral parameter, calibration data derived from the measured calibration dataset describing different receiving spectra is used.

According to one or more of the present embodiments, it is therefore provided to take account of the receiving spectrum received by the X-ray detector. The spectrum is describable with different spectral parameters that are usually known or at least derivable during or through the recording of the image dataset. If a calibration dataset that also describes different receiving spectra and thus enables a selection or derivation of suitable calibration data is now available, highly accurate conversion information taking account of the specific process of recording the image dataset and/or geared to the specific patient may be generated, which therefore leads to a more accurate determination of the at least one physical property value. For example, an irradiation plan, a scoring application, and the like may supply improved information regarding the patient (e.g., at least his scanning region contained in the image dataset).

As is fundamentally known in the prior art, the allocation rule may be or include a look-up table (e.g., conversion table) and/or an imaging function, and/or the conversion information may include free model parameters of a model used for conversion, therefore the look-up table or variables characterizing the imaging function, as is fundamentally known in the prior art. The X-ray apparatus is, for example, a computed tomography apparatus that supplies particularly accurate three-dimensional information, and, therefore, attenuation coefficients (HU values) as image values for voxels defined in three-dimensional space within a patient, with high quality. Due to the conversion information, the correspondingly present image values, available, for example, as HU values, may be converted into physical property values in this voxel (e.g., an electron density, a mass density, and/or a stopping power).

A calibration method is implemented on the X-ray apparatus that uses a pre-defined technical phantom that is suitable for determining the necessary calibration data. For this purpose, the phantom may contain a plurality of (e.g., five) suitable calibration materials that, during the stoichiometric calibration, may include, for example, Teflon and PMMA. The calibration materials may be present in a cylindrical form and are embedded in a cylindrical body consisting of a water-equivalent phantom material. Through measurements with the X-ray apparatus on this phantom, as described in greater detail below, for different spectral parameters, calibration data is recorded as a calibration dataset. The respectively current calibration dataset may be permanently held available on the X-ray apparatus.

If an image dataset of a scanning region of a patient is prepared with special spectral parameters, the calibration dataset may be used in order, following selection or derivation of the suitable calibration data according to the spectral parameters, as is fundamentally known with the presence of calibration data, to derive the suitable conversion information. The use of the present embodiments in a stoichiometric calibration may be provided, although any type of calibration may be used in which, based on calibration data, conversion information that contains or parameterizes an allocation rule may be derived in order to allocate physical target variables (e.g., property values) to an image value of an image dataset.

Overall, with this approach, a simplification of work is fundamentally achieved since it is no longer necessary to acquire calibration data for each individual investigation procedure of a patient. Rather, suitable calibration data may be derived from a more comprehensive calibration dataset based on the spectral parameters of a current investigation procedure. For example, a certain automation is possible herein since, given knowledge of the spectral parameters, a manual selection or maintenance of conversion information may be omitted and thus also a possible error source. In one embodiment, patient-specific conversion information may be generated.

In this context, an embodiment provides that, as the spectral parameter, a, for example, slice-specific extent parameter describing an extent of the patient is used. As the phantom, a phantom including a water-equivalent attenuating phantom material around the at least one calibrating material is used. This provides that in the context of one or more of the present embodiments, it is possible to take account of the filtering effect of the patient on the receiving spectrum in that one of the spectral parameters is an extent parameter of the patient that leads to a corresponding selection of calibration parameters. It is taken into account that the X-ray radiation for recording the image dataset is to pass through the patient, and thus, a water-equivalent transirradiated distance that is defined by the extent of the patient is to be taken into account and in the phantom, may be represented by a corresponding water-equivalent phantom material. In one embodiment, for each slice that is covered by the image dataset, a separate set of conversion information is acquired since the extent of the patient from slice to slice (or sectional image to sectional image) may vary. Thus, by taking account of the patient properties influencing the receiving spectrum, a more exact (e.g., slice-specific) conversion is hereby enabled.

In one embodiment, a phantom with, for each calibration material, a plurality of geometrical extents (e.g., diameters) of the phantom material surrounding the calibration material is used. This provides that in order to be able to reproduce different water-equivalent transirradiated distances for the phantom also, the phantom may have a suitable geometrical configuration in which a plurality of different transirradiated distances of the phantom material are provided. For this purpose, a cylindrical phantom having a stepped outer diameter may be used. In this way, therefore, for different transirradiated distances of the phantom material, which behaves with regard to X-ray absorption as water-equivalent, calibration data is obtained. In one embodiment, for extent parameters of a patient that lie therebetween, interpolations in the calibration data may be carried out. Therefore, the dependency of the image value of the image dataset on the effective water transirradiation distance may already be characterized in the calibration dataset.

The extent parameter may include a mean diameter of the patient, which is used for derivation of the calibration data from the calibration dataset as the diameter of the phantom. A mean effective diameter of the patient has thereby proved to be an extremely accurate estimation with regard to the filter effect over the whole of the projection data entering the image dataset. While an assumption of the patient as an ellipse and a corresponding elliptical configuration of a phantom may be taken into account, this is, however, associated with a significantly greater effort that brings only a relatively slight accuracy improvement. In one embodiment, a mean and therefore effective diameter of the patient may thus be used. If, calibration data for various diameters of the phantom is available, a corresponding selection of calibration data from the calibration dataset, or by interpolation, a calculation of suitable calibration data may take place.

The extent parameter may suitably be determined from the image dataset itself and/or from a topogram recorded for planning the recording of the image dataset. This provides that current information determined in the context of the investigation process is utilized in order to determine the extent parameter (e.g., slice-specifically from mean diameters). This is possible without difficulty by, in a concrete example, a simple segmentation for the sectional images arising (e.g., as part of the image dataset).

In exemplary embodiments, the extent parameter may be estimated from, for example, patient information such as sex, height, weight, BMI, scanning region, and the like.

As previously mentioned, in the context of one or more of the present embodiments, with extent parameters available for each slice of the image dataset, the conversion information is determined slice-specifically. This provides that for each slice and each physical property value, the conversion information contains an allocation rule or specifications (e.g., model parameters) parameterizing the allocation rule. The allocation rule may then determine the at least one physical property value with particularly high accuracy and quality, dependent upon the properties of the mean detected receiving spectrum and thus dependent upon the effective mean water-equivalent transirradiated distance from the image values of the image dataset (e.g., therefore, the HU values). This is achieved by patient-specific conversion information.

In the context of the present embodiments, other spectral parameters that may relate to the X-ray apparatus itself may naturally also be utilized. Thus, a development provides that as a spectral parameter, at least one generating parameter describing the transmitting spectrum generated by an X-ray source (e.g., a tube voltage and/or at least one filter parameter describing at least one filter that is employed) is used. The calibration dataset is measured for a plurality of different generating parameters or filter parameters. Thus, for the different generating parameters and filter parameters, calibration data is available in the calibration dataset or may at least be derived therefrom (e.g., by interpolation). In this way, the properties of the X-ray apparatus are also determined for a plurality of recording parameters relating thereto (e.g., differently usable transmitting spectra or differently usable filter settings) and used for further improving the quality of the physical property values determinable by the conversion information.

As previously indicated, an embodiment of the method provides that for at least one spectral parameter of the image dataset for which no calibration data is available in the calibration dataset, suitable calibration data may be derived by interpolation. This provides that a suitable number of support points are defined for each spectral parameter (e.g., through a stepped formation of the phantom for a plurality of defined diameters of the phantom and/or a plurality of measuring procedures with different generating parameters and/or filter parameters). For further concrete spectral parameters, corresponding calibration data is derived by interpolation from the calibration dataset at these support points and may be utilized for determining the conversion information. In this way, a more accurate determination of the physical property values is provided than on use of the calibration data of the closest support point.

In the context of the method of one or more of the present embodiments, a stoichiometric calibration is used. The free model parameters of a stoichiometric model used for determining the allocation rule are described by the calibration data dependent upon the at least one spectral parameter. For the fundamental description of the stoichiometric calibration, reference is made to the article by Uwe Schneider et al. cited in the introduction. As conversion information, free model parameters may be determined dependent upon the spectral parameters from the calibration data. From this, for example, a corresponding relationship between the free model parameters and the spectral parameters may be derived.

In a development, the conversion information may be determined for a plurality of stoichiometrically described patient materials occurring inside a patient, whereby the number and/or type of the patient materials for which conversion information is determined is restricted and/or defined based on an item of patient information. This provides that the selection of the conversion support points/patient materials does not necessarily need to be firmly defined, but may also be influenced by an item of patient information. For example, the item of patient information includes a scanning region of the image dataset and/or a scanning protocol that is used and/or the age and/or the sex of the patient. The selection may also be influenced by other physiological/anatomical features. In one embodiment, the patient information is determined at least partially automatically by the X-ray apparatus and/or at least partially manually by a user input. If, for example, the X-ray apparatus is capable of recognizing scanned body regions and/or if the patient information may be obtained in other ways (e.g., via a connection to an information system), then at least a part of the patient information may be acquired automatically. It may, however, also be suitable if an operator is capable of exercising influence on the corresponding selection (e.g., restriction) of particular patient materials. In one exemplary embodiment, the operator may directly configure, as user input, the density and the stoichiometric composition of the patient materials, for example, in a suitable user interface.

This configuration therefore ultimately allows the use of prior knowledge regarding the patient or the scanning region of the image dataset. If, as patient information, it is known, for example, that a scan has been carried out in the chest region of a woman, then mammary gland tissue may be covered in the conversion information, whereas for a man, this is unnecessary. Accordingly, in the chest region, tissue types that only occur in the abdominal region may be excluded from the conversion information, which is therefore provided as a whole "made to measure" for the current application case, and thus to the image dataset and the patient. The corresponding configuration in which the number of patient materials to be covered is reduced (e.g., in the case of look-up tables and/or other allocation rules, for the covering of which the quantity of conversion information would significantly increase) is suitable. In the taking into account of patient information as provided, however, the quantity of conversion information may be kept low, which may be suitable, for example, for the transference of conversion information, for example, to a planning device.

In one embodiment, the conversion information is determined at the X-ray apparatus and is transferred together with the image dataset to an evaluating device further evaluating the image dataset. Since the determined conversion information is not only specific to the X-ray apparatus, but also to the specific image dataset/patient, the determined conversion information is suitably already generated by the X-ray apparatus and delivered together with the image dataset to an apparatus connected downstream (e.g., a planning device). Since it is also possible, based on the calibration dataset, to create the conversion information automatically using the X-ray apparatus, manual effort for creating and maintaining conversion information is dispensed with (e.g., by the planning device) since an extended use of existing possibilities of the X-ray apparatus takes place. A possible manual selection of an item of conversion information in the evaluating device (e.g., the planning device) is dispensed with so that a possible error source is no longer present. With that, a distinct lightening of the workload is provided.

In one embodiment, on the part of the X-ray apparatus, the physical property values may be created as a property dataset in addition to the image data set, and the property dataset may be transferred to the evaluating device. However, this is less preferable since users tend toward receiving an image dataset for observing and tend to decline further datasets (e.g., the property dataset) that do not have any observational purpose. In addition, the quantity of the data to be transferred is significantly reduced, and the physical property values may, if needed, be determined on site in the evaluating device (e.g., the planning device) based on the conversion information. This is particularly suitable if the physical property values are only needed in particular regions of the image dataset, or the like.

The conversion information may also include information regarding for which physical property values the allocation rules/model parameters accordingly included are suitable.

In one embodiment, the conversion information may be added to the image dataset as metadata (e.g., as DICOM metadata), and/or the image dataset may be transferred processed by evaluation for contrast optimization with regard to a representation. In one embodiment, the conversion information may be added to the image dataset as metadata and therefore form, on the side of the evaluating device, an integral part of the image dataset or of the corresponding data object, so that a direct access in a defined manner takes place and the physical property values may be determined particularly easily. In the DICOM format, a free space is already provided for metadata defined on the user side, which may suitably be used for the conversion information.

In one embodiment, the image dataset is contrast-optimized for imaging purposes. A further marked advantage is thereby provided over, for example, a procedure that directly provides visual images of the physical property values to the evaluating device. For example, in a planning device as an evaluating device, it is possible without difficulty to use the image dataset further for imaging purposes (e.g., to conclude the position of the treatment region, such as a tumor, from the image values of the image dataset and to incorporate the position accordingly in the planning). The physical property values may then be determined rapidly and easily when needed, in the example of dose calculation, based on the conversion information also supplied. During the conversion of image datasets into physical property values, contrast losses may occur since, for example, an electron density has a lower contrast dynamic than commonly-used attenuation coefficients. Since the image dataset optimized for the imaging is transferred together with the conversion information, the advantages of both data forms may be provided unified in a compact manner.

The determination of the conversion information does not necessarily have to take place in the X-ray apparatus itself, but, for example, an intermediate device, to which the image dataset is transferred and which has access to the calibration dataset, may also be used. The intermediate device determines the conversion information and may add the conversion information to the image dataset, possibly as metadata, in order to pass the image dataset on to the evaluating device. Distributed determinations of the conversion information may also be provided. Spectral parameters relating to the X-ray apparatus (e.g., generating parameters and/or filter parameters) are in any case mostly stored, on use of the DICOM format, within the corresponding data object of the image dataset and are thus also available at other locations.

In one embodiment, the method may be utilized in radiation therapy planning (e.g., particle therapy planning). It may thus be provided that the conversion information may be used for a radiation therapy planning, and, for example, the evaluating device is a planning device of a planning system. Particularly in particle therapy (e.g., in irradiation with protons or heavy ions), a high degree of accuracy of the determination of the physical property values (e.g., of a stopping power, an electron density, and/or a mass density) is important in order to be able to provide the treatment success as extensively as possible.

Suitably, the measuring of the calibration dataset may be repeated cyclically (e.g., in maintenance intervals). As part of regular quality assurance measures on the X-ray apparatus (e.g., between daily and annually), the calibration scan may be undertaken with the phantom. After this, the respective current calibration dataset is stored. Thus, in the event of changes to the X-ray apparatus, suitable calibration data is always present in the calibration dataset.

In one embodiment, apart from the introduction of the phantom by an operator, the measurement of the calibration dataset may be carried out by the X-ray apparatus entirely automatically according to a calibration program. For example, the phantom may thus be mounted by the operator on and/or at a patient support of the X-ray apparatus. Thereupon, the X-ray apparatus may position the phantom automatically, and in a further act, may carry out suitable X-ray scans on the phantom (e.g., at different generating parameters and/or filter parameters), for which purpose the calibration program is used. The measuring results are then evaluated in order to determine the image values of all the calibration materials situated in the phantom, spectrum-dependently, which may also relate to different diameters of the phantom. The calibration dataset results from this. In one embodiment, the at least respectively current calibration dataset is stored in a database of the X-ray apparatus. Since the calibration dataset is valid for different spectral parameters, the calibration dataset may thus be applied to a plurality of scans with the X-ray apparatus, so that a scan of the phantom does not have to take place first before every recording of an image dataset.

It should also be noted that the inventive method is naturally also transferable to multi-energy computed tomography or spectral imaging. In this case, the corresponding allocation rules allocate a physical property value to at least two image values (of the different energies/transmitting spectra).

In addition to the method, the present embodiments also relate to an X-ray apparatus (e.g., a computed tomography apparatus) including a recording device. The recording device includes a recording apparatus including an X-ray detector and an X-ray source. The X-ray apparatus also includes a control device configured for carrying out the method according to the present embodiments. All the embodiments relating to the method may be transferred analogously to the X-ray apparatus with which the above mentioned advantages may therefore also be achieved. The control device may include at least one processor and at least one storage device, by which, for example, a database for storing the calibration dataset is realized. In addition to a recording unit that, as known in principle, controls the recording or scanning operation of the X-ray apparatus and may also be used for recording the calibration dataset and the image dataset, the control device may include, for example, a conversion information determining unit in order to use the spectral parameters and to determine the suitable conversion information. Further functional units according to described possible acts of the method may also be provided.

An computer program of one or more of the present embodiments is, for example, directly loadable into a memory store of a computer device (e.g., of a control device of an X-ray apparatus), and/or an intermediate device, and is configured to carry out the acts of a method when the computer program is executed in the computer device. The computer program may be stored on an electronically readable data carrier (e.g., a non-transitory computer-readable storage medium), which therefore includes electronically readable control information stored thereon. This includes at least one computer program of one or more of the present embodiments and is configured such that, on use of the data carrier in a control device, the control information carries out a method. The data carrier may be a non-transient data carrier (e.g., a CD-ROM).

DETAILED DESCRIPTION

Figure 1:
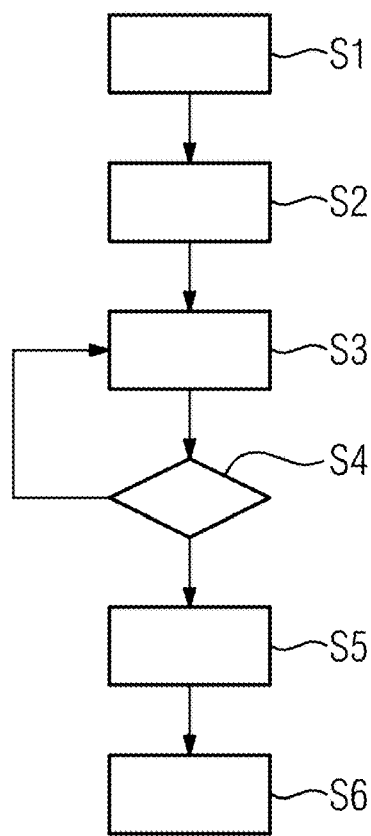
FIG. 1 is a flow diagram of an exemplary embodiment of a method in a calibration phase.
Figure 3:
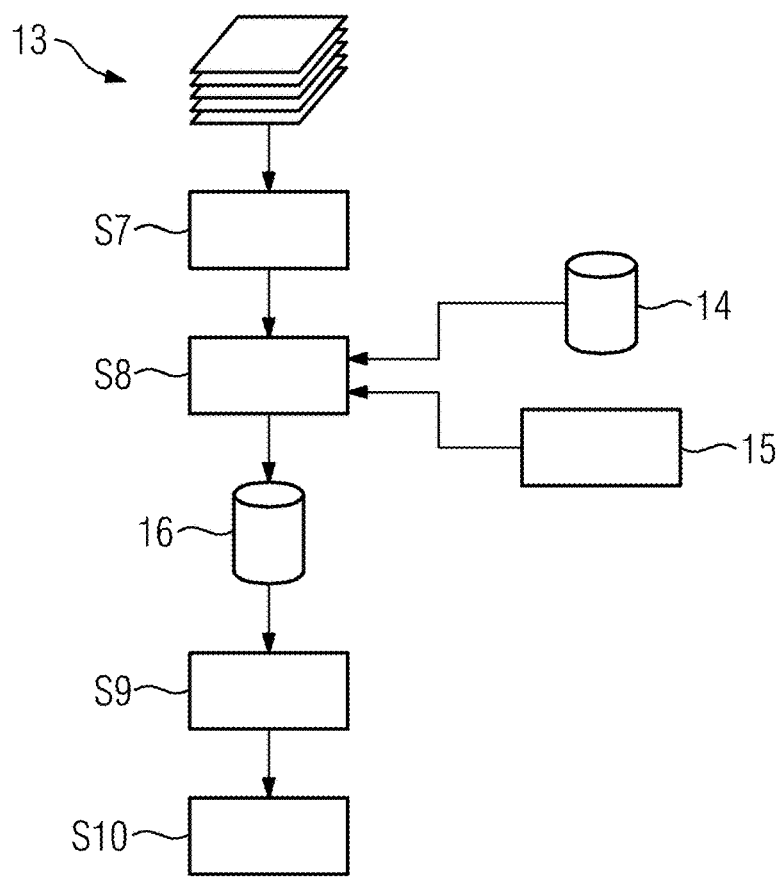
FIG. 3 is a flow diagram of an exemplary embodiment of the method in a conversion information determination phase.

The flow diagrams in FIGS. 1 and 3 show, for an exemplary embodiment of the method, how the method may be used for preparing a radiation therapy plan. FIG. 1 concerns acts for generating a calibration dataset in a calibration phase, where the corresponding calibration dataset may be used for a plurality of subsequent actual investigation processes of a patient with the corresponding X-ray apparatus, whereby a corresponding use of the calibration dataset that is stored in a database of the X-ray apparatus will be described in greater detail according to FIG. 3.

The calibration phase shown in FIG. 1 is repeated cyclically, for example, in typical maintenance intervals that may vary from daily to annually. In act S1, a specially designed phantom is fastened on a patient support of the X-ray apparatus by an operator.

Figure 2:
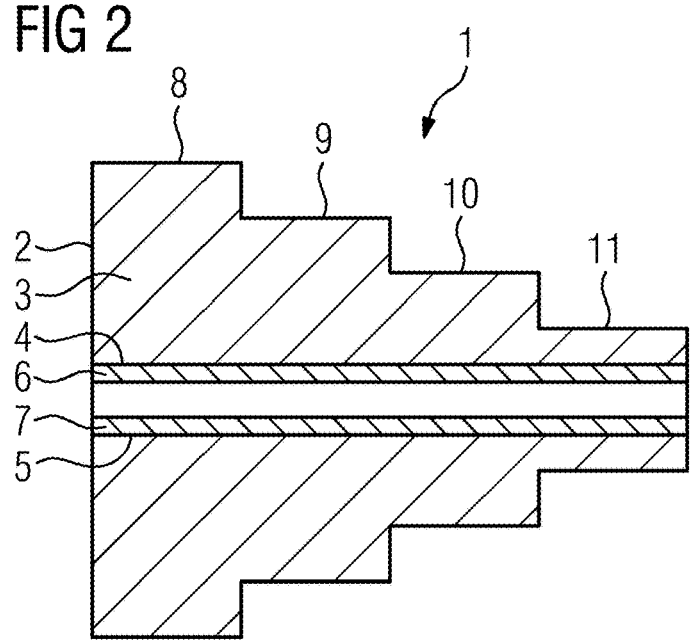
FIG. 2 is an example of a usable phantom.

FIG. 2 shows a possible embodiment of such a phantom 1 in more detail. The phantom 1 has a cylindrical base body 2 made of a phantom material 3 stepped in a plurality of diameters. The phantom material 3 behaves with regard to the attenuation of X-ray radiation substantially equivalent to water. Embedded within the phantom material 3 there are also cylindrically shaped calibration material bodies 4, 5 each made of a calibration material 6, 7. Typically, more than one calibration material (e.g., five calibration materials) suitable for a stoichiometric calibration is used. For example, the calibration material 6 may be Teflon, and the calibration material 7 may be PMMA.

The calibration dataset to be generated in the calibration phase is to be suitable for different spectral parameters describing the receiving spectrum received by the X-ray detector of the X-ray apparatus. The stepped embodiment with the different diameters in the regions 8, 9, 10 and 11 of the phantom 1 is aimed at an extent parameter describing the extent of a patient, since in the further procedure, an effective diameter of the patient is used. Since the phantom 1 in the present case may be substantially measured entirely, different measurements for different diameters are dispensed with, since these are already given by the corresponding geometric design of the phantom 1. Since the phantom material 3 is water-equivalent, the different diameters in the regions 8 to 11 may be understood as analogous to water-equivalent transirradiated distances of the patient.

Following the mounting of the phantom 1 on the patient support, in act S2, a calibration program is started by the operator. With the start of the calibration program, the X-ray apparatus autonomously suitably positions the phantom 1, and in act S3, the X-ray apparatus carries out a first calibration scan of the phantom 1. A set of particular pre-defined X-ray apparatus-related spectral parameters that may include the generating parameter describing the generating spectrum generated by the X-ray source (e.g., a tube voltage, and/or filter parameters describing the filters used, and/or corresponding settings) is used. The scan results are initially stored.

In act S4, it is checked whether scans for further sets of X-ray apparatus-specific spectral parameters are pending. If this is the case, for the next set of pre-defined spectral parameters to be measured, a return to act S3 takes place. Otherwise, if all the scan results are available, the process continues at act S5.

In act S5, the scan results of the acts S3 are evaluated in order to obtain a calibration dataset. Since a stoichiometric calibration is to be used in the present case, a stoichiometric model parameterized by free model parameters that links image values (e.g., actual HU values dependent upon the density and stoichiometric composition of a material) with a physical property value, and thus defines an allocation rule. As the one or the plurality of physical property values, for example, an electron density, a mass density, and a stopping power may be utilized.

The free model parameters depend on the spectral parameters. Since the stoichiometric composition and the corresponding densities of the calibration materials 6, 7 are known and from the scan results, image values for different spectral parameters are available, in the evaluation in act S5, a relationship between the model parameters and the spectral parameters may be derived. Through interpolation, calibration data or a complete imaging rule may also be achieved for values of the spectral parameters between the measured values, so that the calibration data of the calibration dataset formed, which is stored permanently in a storage medium of the X-ray apparatus in act S6, specifically in a database, finally describes the change of the model with a changed receiving spectrum.

Figure 4:
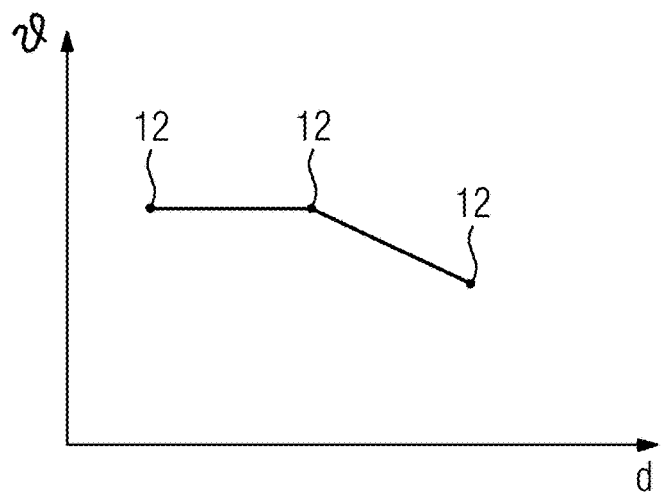
FIG. 4 is a possible dependency of a model parameter on a spectral parameter.

FIG. 4 shows an exemplary relationship of a model parameter $\square$ and a spectral parameter (e.g., the water-equivalent transirradiated distance d), whereby scan points 12 of the calibration scan and the interpolation lying therebetween are indicated.

FIG. 3 shows in more detail how the calibration dataset is used in an actual examination procedure of a patient. Since in the present case the X-ray apparatus is a computed tomography apparatus, the three-dimensional image dataset 13 exists following the recording and the reconstruction, as is known in principle, as an image stack of sectional images or slice images (e.g., for different slices of the patient). The image dataset 13 is thereby available as a DICOM data object, so that recording parameters used as spectral parameters are also contained in this data object as metadata (e.g., generating parameters describing the generating spectrum). In order to acquire conversion information within the meaning of the stoichiometric calibration, in act S7, by evaluating the image dataset 13, for each slice, the extent parameter of the patient is determined (e.g., as the mean diameter). Alternatively to an acquisition from the respective slice images of the image stack, the extent parameter may be determined slice-specifically from topograms recorded for preparing for the recording of the image dataset 13.

Once the extent parameter has been determined as a spectral parameter in act S7, all the spectral parameters are thus available so that in act S8, the conversion information may be compiled slice-specifically (e.g., based on the slice-specific conversion information), for which purpose the calibration dataset 14 and additionally an item of patient information 15 are taken into account.

The patient information 15 describes, for example, the scanning region, the sex, and/or other physiological/anatomic features of the patient and finally serves to determine patient materials covered through the conversion information. Thus, for example, the conversion information may be restricted to tissue types actually occurring in the scanning region. The patient information 15 may be determined at least partially by the X-ray apparatus itself, but also by a user using a user input. In one embodiment, a user interface in which the user may specifically configure the density and stoichiometric composition of the patient material sensitivity in order to be suitable for special cases may be used.

Since therefore in act S8 the model parameters for the corresponding spectral parameters are then known slice-specifically from the calibration data of the calibration dataset 14 or may be derived therefrom, and it may be determined for which patient materials conversion information is to be provided, the conversion information may be gathered in the context of the usual stoichiometric calibration (e.g., as the free model parameters to be used and densities/stoichiometric data of the patient materials); it is, however, also possible to acquire immediately the corresponding allocation rule (e.g., as a look-up table (conversion table)) and to determine the allocation rule as conversion information.

The result is patient information, X-ray apparatus information, and, based upon the consideration of the water-equivalent transirradiated distance, even slice-specific conversion information 16 that is added in act S9 as metadata to the image dataset 13. This is easily possible in the DICOM format, which is used here. The thus enhanced data object of the image dataset 13 is provided in act S10 by the X-ray apparatus to a corresponding evaluating device (e.g., a planning device). Since the image dataset 13 is still retained in a contrast-optimized form for the imaging, with the image values (HU values), a representation for irradiation planning may take place without difficulty (e.g., with localization of the actual planning region targeted as the goal, such as a tumor). Due to the also supplied conversion information 16, however, a dose distribution calculation may take place highly accurately and rapidly, so that the planning overall may take place simply and with provision of a compact information packet.

Figure 5:
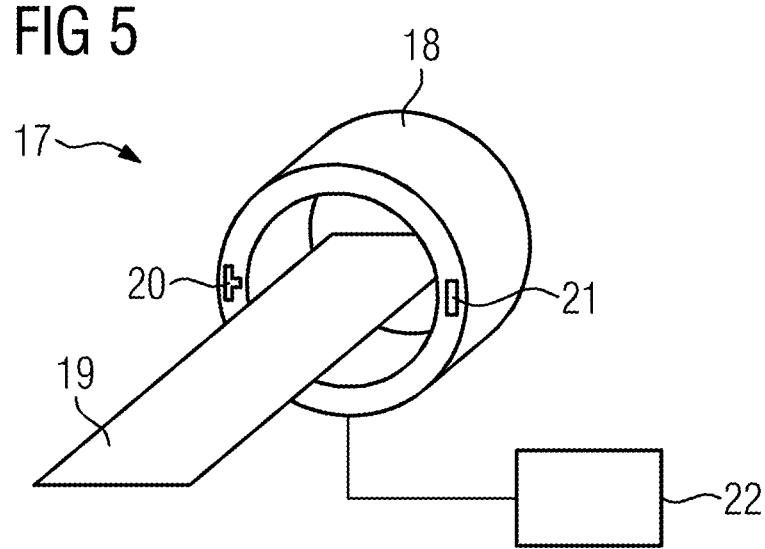
FIG. 5 is an embodiment of an X-ray apparatus.

FIG. 5 shows a sketch of the principle of one embodiment of an X-ray apparatus 17 (e.g., a computed tomography apparatus) that includes, as known in principle, a gantry 18, in which a patient (or the phantom 1) may be moved by a patient support 19. Arranged rotatably within the gantry is a scanning arrangement with an X-ray source 20 and an X-ray detector 21 in order to produce projection images of the corresponding scanning region to be recorded of the patient. In a known manner, image datasets 13 or corresponding attenuation coefficients may be derived from the projection images as image values.

The operation of the X-ray apparatus 17 is controlled by a control device 22 that is also configured for carrying out one or more embodiments of the method. This provides that in this case, the X-ray apparatus 17 itself provides complete DICOM data objects with the image dataset 13 and the appropriate conversion information 16. In alternative configurations, an intermediate device that determines the conversion information 16 and/or a distributed determination of the conversion information 16 may be provided.

Figure 6:
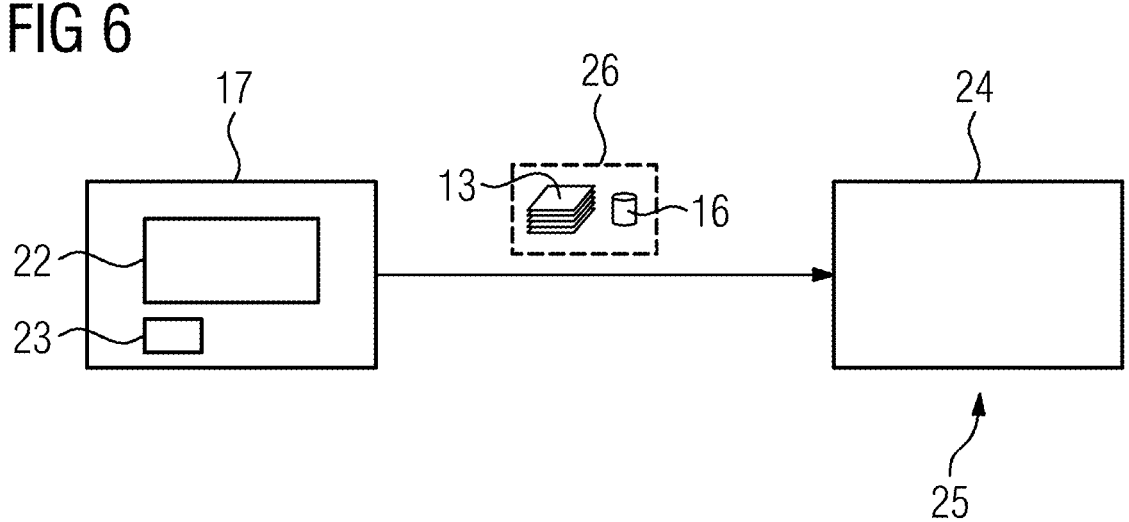
FIG. 6 is a possible embodiment of a planning system for radiation therapy.

FIG. 6 shows one embodiment of a complete treatment system for therapy planning to which, apart from the X-ray apparatus 17 with the control device 22 and the database 23, also indicated here, for storing the calibration dataset 14, a planning device 24 as an evaluating device 25 belongs. The DICOM data object 26 with the image dataset 13 and the conversion information 16 is provided to the planning device 24 by the X-ray apparatus 17 via a corresponding communication connection.

The complete provision of the image dataset enhanced with conversion information as metainformation by the X-ray apparatus directly to an evaluating device itself represents an advantageous embodiment that may also advantageously be used independently of the spectral parameter dependency.

Although the invention has been illustrated and described in detail with the exemplary embodiments, the invention is not restricted by the examples given, and other variations may be derived therefrom by a person skilled in the art without departing from the protective scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for providing an item of conversion information describing an allocation rule of at least one physical property value of a material in a voxel relating to an image value of the voxel in a three-dimensional (3D) image dataset recorded with an X-ray apparatus, the method comprising:

determining a calibration dataset that is used for determining the allocation rule, the determining of the calibration dataset comprising scanning a phantom in the X-ray apparatus, the phantom comprising at least one calibration material, wherein the 3D image dataset is recorded with a receiving spectrum geared to an X-ray detector of the X-ray apparatus, the receiving spectrum being described by at least one spectral parameter; and determining the allocation rule dependent upon the at least one spectral parameter, the determining of the allocation rule comprising using calibration data derived from the determined calibration dataset describing different receiving spectra, wherein the at least one spectral parameter includes a slice-specific extent parameter describing an extent of the patient, and wherein the at least one physical property value represents an electron density, a mass density, a stopping power, or any combination thereof.

2. The method of claim 1, wherein the phantom is a phantom including a water-equivalent attenuating phantom material around the at least one calibration material.

3. The method of claim 2, wherein the phantom is a phantom with, for each calibration material of the at least one calibration material, a plurality of geometrical extents of the water-equivalent attenuating phantom material surrounding the respective calibration material.

4. The method of claim 3, wherein the plurality of geometrical extents are diameters.

5. The method of claim 2, wherein the slice-specific extent parameter comprises a mean diameter of the patient, and
wherein the mean diameter of the patient is used for selection of the calibration data as the diameter of the phantom.

6. The method of claim 2, wherein the slice-specific extent parameter is determined from the image dataset, from a topogram recorded for planning the recording of the image dataset, or from a combination thereof.

7. The method of claim 2, wherein with an extent parameter available for each slice of the image dataset, the conversion information is determined slice-specifically.

8. The method of claim 1, wherein the at least one spectral parameter comprises at least one generating parameter describing a transmitting spectrum generated by an X-ray source, and
wherein the calibration dataset is determined for a plurality of different generating parameters or filter parameters.

9. The method of claim 8, wherein the at least one generating parameter comprises a tube voltage, at least one filter parameter describing at least one filter that is employed, or the tube voltage and the at least one filter parameter.

10. The method of claim 1, wherein for at least one spectral parameter of the 3D image dataset for which no calibration data is available in the calibration dataset, calibration data is derived by interpolation.

11. The method of claim 1, wherein a stoichiometric calibration is used, and
wherein free model parameters of a stoichiometric model used for determining the allocation rule are described by the calibration data dependent upon the at least one spectral parameter.

12. The method of claim 11, further comprising determining the conversion information for a plurality of stoichiometrically described patient materials occurring inside a patient,
wherein a number, a type, or a number and a type of the patient materials for which the conversion information is determined is restricted, defined, or restricted and defined based on an item of patient information.

13. The method of claim 12, wherein the patient information is determined at least partially automatically by the X-ray apparatus, is determined at least partially manually by a user input, comprises a scanning region of the image dataset, a scanning protocol that is used, an age of the patient, a sex of the patient, or comprises any combination thereof, or any combination thereof.

14. The method of claim 1, further comprising determining the conversion information at the X-ray apparatus and transferring the conversion information together with the image dataset to an evaluating device further evaluating the image dataset.

15. The method of claim 14, wherein the conversion information is addable to the image dataset as metadata, the image dataset is transferred processable by evaluation for contrast optimization with regard to a representation, or a combination thereof.

16. The method of claim 1, wherein the determining of the calibration dataset is repeatable cyclically, is carried out entirely automatically according to a calibration program by the X-ray apparatus, the respective current calibration dataset is stored in a database of the X-ray apparatus, or any combination thereof.

17. The method of claim 16, wherein the determining of the calibration dataset is repeatable cyclically in maintenance intervals, apart from introduction of the phantom by an operator, or in maintenance intervals and apart from introduction of the phantom by the operator.

18. An X-ray apparatus comprising:
a recording device comprising:
an X-ray detector; and
an X-ray source; and
a controller configured to provide an item of conversion information describing an allocation rule of at least one physical property value of a material in a voxel relating to an image value of the voxel in a three-dimensional (3D) image data set recorded with the X-ray apparatus, the provision of the item of conversion information comprising:
determination of a calibration dataset that is used for determining the allocation rule, the determination of the calibration dataset comprising scanning a phantom in the X-ray apparatus, the phantom comprising at least one calibration material, wherein the 3D image data set is recorded with a receiving spectrum geared to an X-ray detector of the X-ray apparatus, the receiving spectrum being described by at least one spectral parameter; and
determination of the allocation rule dependent upon the at least one spectral parameter, the determination of the allocation rule comprising use of calibration data derived from the determined calibration dataset describing different receiving spectra,
wherein the at least one spectral parameter includes a slice-specific extent parameter describing an extent of the patient, and
wherein the at least one physical property value represents an electron density, a mass density, a stopping power, or any combination thereof.

19. In a non-transitory computer-readable storage medium that stores instructions executable by a computer to provide an item of conversion information describing an allocation rule of at least one physical property value of a material in a voxel relating to an image value of the voxel in a three-dimensional (3D) image data set recorded with an X-ray apparatus, the instructions comprising:

determining a calibration dataset that is used for determining the allocation rule, the determining of the calibration database comprising scanning a phantom in the X-ray apparatus, the phantom comprising at least one calibration material, wherein the 3D image data set is recorded with a receiving spectrum geared to an X-ray detector of the X-ray apparatus, the receiving spectrum being described by at least one spectral parameter; and determining the allocation rule dependent upon the at least one spectral parameter, the determining of the allocation rule comprising using calibration data derived from the determined calibration dataset describing different receiving spectra, wherein the at least one spectral parameter includes a slice-specific extent parameter describing an extent of the patient, and wherein the at least one physical property value represents an electron density, a mass density, a stopping power, or any combination thereof.

* * * * *